United States Patent
Correia et al.

(10) Patent No.: US 7,127,933 B2
(45) Date of Patent: Oct. 31, 2006

(54) HIGH SPEED RESILIOMETER

(75) Inventors: Diomar Correia, Achusnet, MA (US); Michael McNamara, Fairhaven, MA (US); Laurent C. Bissonnette, Portsmouth, RI (US); David A. Bulpett, Boston, MA (US)

(73) Assignee: Acushnet Company, Fairhaven, MA (US)

( * ) Notice: Subject to any disclaimer, the term of this patent is extended or adjusted under 35 U.S.C. 154(b) by 9 days.

(21) Appl. No.: 10/914,289

(22) Filed: Aug. 10, 2004

(65) Prior Publication Data

US 2006/0032288 A1     Feb. 16, 2006

(51) Int. Cl.
*G01M 7/00* (2006.01)
(52) U.S. Cl. .................................... 73/12.11
(58) Field of Classification Search ............. 73/12.01, 73/12.11; 273/121.1
See application file for complete search history.

(56) References Cited

U.S. PATENT DOCUMENTS

| | | | |
|---|---|---|---|
| 3,093,995 A | 6/1963 | Gordon | |
| 3,364,751 A | 1/1968 | Cornell et al. | |
| 3,509,736 A | 5/1970 | Saari | |
| 3,677,546 A | 7/1972 | Oetiker | 273/102.2 |
| 3,814,438 A | 6/1974 | Baron et al. | 273/176 |
| 3,999,756 A | 12/1976 | Head | 463/64 |
| 4,071,242 A | 1/1978 | Supran | 273/61 |
| 4,289,023 A | 9/1981 | Rader | 73/12.09 |
| 4,448,417 A * | 5/1984 | Clark et al. | 273/121 A |
| 4,870,868 A | 10/1989 | Gastgeb et al. | 73/649 |
| 4,928,965 A | 5/1990 | Yamaguchi et al. | 473/332 |
| 5,221,082 A | 6/1993 | Curchod | 273/185 |
| 5,245,862 A | 9/1993 | Zeiss | 73/79 |
| 5,419,565 A | 5/1995 | Gordon et al. | 273/374 |
| 5,437,457 A | 8/1995 | Curchod | 273/185 |
| 5,626,526 A | 5/1997 | Pao et al. | 473/156 |
| 5,672,809 A | 9/1997 | Brandt | 73/12.01 |
| 5,682,230 A | 10/1997 | Anfinsen et al. | |
| 5,703,294 A | 12/1997 | McConnell et al. | 73/579 |
| 5,803,832 A | 9/1998 | Nakamura et al. | 473/377 |
| 5,846,139 A | 12/1998 | Bair et al. | 473/156 |
| 5,863,255 A | 1/1999 | Mack | 473/152 |

(Continued)

*Primary Examiner*—Jewel Thompson
(74) *Attorney, Agent, or Firm*—Bingham McCutchen LLP (57) ABSTRACT

An apparatus and method for testing the physical properties of a material is disclosed. Preferably, the physical properties that may be tested include, but are not limited to, the COR of a material. Accordingly, the apparatus includes a projectile that may be capable of being propelled towards a material sample. The projectile is preferably aimed and fired through a tubular barrel towards the material sample. The tubular barrel preferably comprises a propulsion system that controls pneumatic energy via a pneumatic valve. At least two sensors are placed between the tubular barrel and the material sample in order to detect the passage of the projectile. It is desired that the sensors are placed at precise, discrete positions. As the projectile passes through the field of view of each sensor, the time is recorded to a memory, for example, a counter timer board. The projectile may then impact the material sample, which may preferably be held in place by a fixation device. The fixation device is preferably a holding slot, which may be backed by an infinite mass cylinder. Upon rebounding from the material sample, the projectile passes back through the field of view of the sensors in reverse order, allowing the sensors to capture and record the time of passage to a memory, such as a counter timer board. The physical properties of the material sample may be calculated by a processing device that is operatively connected to at least a portion of the apparatus.

40 Claims, 5 Drawing Sheets

U.S. PATENT DOCUMENTS

| | | | |
|---|---|---|---|
| 6,165,081 A | 12/2000 | Chou | 473/329 |
| 6,289,735 B1 | 9/2001 | Dister et al. | 73/579 |
| 6,354,962 B1 | 3/2002 | Galloway et al. | |
| 6,385,559 B1 | 5/2002 | Boehm | 473/223 |
| 6,571,600 B1 | 6/2003 | Bissonnette et al. | 73/12.02 |
| 6,605,007 B1 | 8/2003 | Bissonnette et al. | 473/329 |
| 6,709,344 B1 | 3/2004 | Erickson et al. | 473/282 |
| 6,769,287 B1 * | 8/2004 | Stewart et al. | 73/12.01 |

* cited by examiner

HIGH SPEED RESILIOMETER

FIELD OF THE INVENTION

The present invention relates to an apparatus and method for determining the physical properties of a material. More specifically, the present invention relates to an apparatus and method for efficiently measuring the coefficient of restitution and contact time for a collision between a projectile with known material properties and a material sample with unknown material properties.

BACKGROUND OF THE INVENTION

The manufacturing of golf clubs and balls requires extensive testing to determine which equipment will prove most advantageous for golf players. Many tests are performed during the designing of equipment in order to determine which materials are best suited for a particular piece of equipment, such as a club or ball. Testing the properties of a particular type of material enables designers to determine the best mode of applying these materials as well as potential product performance advantages.

To determine the properties of different materials, manufacturers have employed many different testing machines. Due to the high rate of deformation associated with golf ball use, these testing machines involve forming a sample of a material and firing it towards a flat surface, such as an immovable plate. These machines often fire the sample out of a firing mechanism, towards the immovable plate. The sample then strikes the immovable plate and rebounds off of it. A sensing system is typically placed in between the firing mechanism and the immovable plate to record the flight of the sample. Based on the output of the sensing system, the properties of the collision, such COR, and contact duration are measured and material characteristics such as elastic modulus and resiliency may be determined.

Existing testing machines, such as the one described above, have many drawbacks. For example, in order to cause the sample to rebound off the immovable plate in a predictable manner, it is often necessary to manufacture a substantially spherical sample. Manufacturing a spherical sample of a material may require specialized molds, unique degassing equipment, or large material quantities, and thus complicates and increases the cost of material tests. These methods are also more time consuming because they require the uniquely molded material sample to be formed according to strict specifications. Furthermore, these testing machines require a new spherical sample to be manufactured if an existing one is deformed in any way, such as by chipping, cracking, tearing, or change in sphericity.

Thus, a continuing need exists for a testing machine that is capable of repeatedly and reliably testing the physical properties of a material without being susceptible to the strict specifications required for material samples used in prior testing machines. A need also exists for an apparatus which does not require a large volume of sample material for test specimen production.

SUMMARY OF THE INVENTION

The present invention comprises an apparatus that substantially minimizes the drawbacks associated with prior testing machines. The present invention comprises an apparatus and method for testing the physical properties of a material. The characteristic properties that may be measured include, but are not limited to, the COR and contact time at various deformation rates and magnitudes of a material. Accordingly, the present invention comprises a projectile that is capable of being propelled towards a material sample. This is in contrast to prior COR testing apparatus that fired a spherical sample of a material at an immovable wall. The projectile is preferably aimed and fired through a tubular barrel towards the material sample. The tubular barrel preferably comprises a propulsion system that controls compressed air via a pneumatic valve. At least two sensors are placed between the tubular barrel and the material sample in order to detect the passage of the projectile. It is desired that the sensors are placed at precise, discrete positions. As the projectile passes through the field of view of each sensor, the time is recorded to a memory, for example, a counter timer board. The projectile may then impact the material sample, which may preferably be held in place by a fixation device. The fixation device preferably includes a drop in slot for the material sample. One side of the material sample may be exposed by a hole, opening, or the like. Preferably, the side exposed by the hole is facing the tubular barrel such that the projectile may impact it. The other side of the material sample may be backed by a mass plate which may be selectively positioned behind the sample. In another embodiment, the fixation device may comprise a v-grove clamp backed by a cylinder. Upon rebounding from the material sample, the projectile passes back through the field of view of the sensors in reverse order, allowing the sensors to capture and record the time of passage to a memory, such as a counter timer board.

It may be desirable to operatively connect a processing device to at least part of the apparatus, such as the sensors. The processing device is preferably capable of housing the memory and a processor that is capable of determining the COR and contact time of the material sample, based on the times recorded by the sensors. The present invention allows the COR of the material sample to be tested based on a reusable projectile. Furthermore, the present invention may accommodate material samples of various shapes and dimensions. This substantially simplifies the testing process by reducing the time and cost associated with forming the material sample. The present invention may also be capable of being used to measure resilience gradients of anisotropic material specimens. This may be accomplished by targeting different locations on the material specimens. Different locations on the material sample may be targeted by moving the sample, moving the tubular barrel, or moving both. The present invention provides the added benefit of occupying a smaller amount of space than prior apparatus by minimizing the distance between the tubular barrel and the material sample.

In one embodiment, the present invention comprises an apparatus for determining the physical properties of a material. The apparatus may include a holding device that is capable of receiving and holding a stationary material sample and a projectile. Also included is a propulsion device that is capable of propelling the projectile towards the stationary material sample. At least two sensors may be selectively positioned between the propulsion device and the stationary material sample. In a preferred embodiment, three or more sensors are used. In some embodiments, the propulsion device may comprise a pneumatic valve. The sensors are preferably proximity sensors which provide a signal when an object is within a planar sensing field. In some embodiments, a processing device may be operatively connected to the sensors in order to determine desired physical properties of the material sample.

In one embodiment, the projectile comprises a metallic sphere. Preferably, the diameter of the sphere is between about 0.0625" and about 0.5". More preferably, the diameter of the sphere may be between about 0.0625" and about 0.25". In order to prevent the sphere from deformation, the elastic modulus of the projectile is preferably substantially greater than the elastic modulus of the sample. Preferably, the ratio of the elastic modulus of the projectile to the elastic modulus of the material sample is greater than about 50:1.

In one embodiment, at least one sensor is positioned less than about 6" from the material sample. In order to allow the material sample to absorb the impact of the projectile, the material sample is preferably supported by a piston or plate whose mass is at least 100 times greater than the projectile.

In another embodiment, the present invention comprises a method for determining one or more physical properties of a material. The method includes providing a stationary material sample, firing an object at the stationary material sample, and determining the inbound and outbound characteristics of the flight of the object. The method further includes correlating the ratio of inbound and outbound characteristics to a property of the stationary material sample. In one embodiment, the object is preferably fired at the sample at a velocity between about 25 fps and 300 fps. More preferably, the object is fired at the sample at a velocity between about 50 and 250 fps. In one embodiment, the inbound and outbound characteristics comprise the velocity of the object. In other embodiments, the inbound and outbound characteristics may comprise the time of passage of the object.

In yet another embodiment, the present invention comprises a method for determining the resiliency of a material. The method includes selectively positioning a stationary material sample at a predetermined distance from at least two sensors responsive to the presence of the projectile. The method also includes propelling a projectile towards the stationary material sample and determining the resiliency of the stationary material sample based on the at least two sensors and the projectile.

Preferably, the projectile is propelled towards the material sample at a velocity between about 25 fps and 300 fps. More preferably, the projectile is propelled towards the material sample at a velocity between about 50 and 250 fps. In one embodiment, the resiliency of the material sample is determined based on the velocity of the projectile. In other embodiments, the resiliency of the material sample is based on the time of passage of the projectile. In one embodiment, the at least two sensors are responsive to the presence of the projectile based on optical sensing. In another embodiment, the at least two sensors are responsive to the presence of the projectile based on magnetic variations. In other embodiments, the at least two sensors are responsive to the presence of the projectile based on capacitance variations. In yet another embodiment, the time and position of the projectile are determined by means of a digital camera.

DETAILED DESCRIPTION OF THE PREFERRED EMBODIMENTS

Prior methods and apparatus for measuring the physical properties, such as resiliency or Coefficient of Restitution (COR) of a material, have involved large apparatus and samples that require arduous preparation. These apparatus may be used in many applications including, but not limited to, the testing of golf equipment. Apparatus for testing the COR of materials are often used in testing candidate material for golf balls. As such, prior COR testing apparatus typically require molding thermoset or thermoplastic materials into a spherical sample. These apparatus often have several drawbacks such as, for example, requiring a costly apparatus to mold the spherical sample and large volumes of sample material to produce an adequate quality and quantity of specimens. In addition, the COR testing apparatus typically requires a large area through which the spherical sample can be fired at a substantially immovable wall. Furthermore, firing spherical samples does not allow for testing the anisotropic properties of a material, such as a golf ball core or component. Either separately, or in combination, the features of prior COR testing apparatus allow for many areas of improvement.

Figure 1:
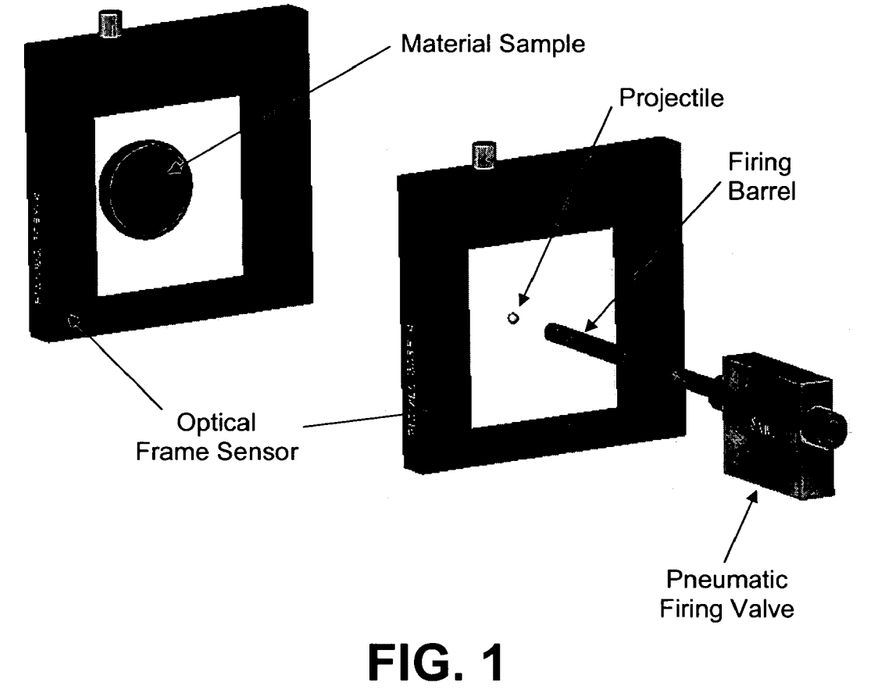
FIG. 1 is a diagram showing an overview of an exemplary embodiment of the present invention.

As shown in FIG. 1, the present invention comprises an apparatus that substantially minimizes the drawbacks associated with prior testing machines. The present invention comprises an apparatus and method for testing the physical properties of a material. The properties of collision that may be measured include, but are not limited to, the COR of a material and contact time. Accordingly, the present invention comprises a projectile that is capable of being propelled towards a material sample. This is in contrast to prior COR testing apparatus that fired a spherical sample of a material at an immovable wall. The projectile is preferably aimed and fired through a tubular barrel towards the material sample. The tubular barrel preferably comprises a propulsion system that controls pneumatic energy via a pneumatic valve. At least two sensors are placed between the tubular barrel and the material sample in order to detect the passage of the projectile. It is preferable that the sensor positions relative to the sample are precisely known. As the projectile passes through the field of view of each sensor, the time is recorded to a memory, for example, a counter timer board. The projectile may then impact the material sample, which may preferably be held in place by a fixation device. The fixation device preferably includes a drop in slot for the material sample. One side of the material sample may be exposed by a hole, opening, or the like. Preferably, the side exposed by the hole is facing the tubular barrel such that the projectile may impact it. The other side of the material sample may be backed by a mass plate which may be selectively positioned behind the sample. In another embodiment, the fixation device may comprise an automated pneumatic clamp. Upon rebounding from the material sample, the projectile passes back through the field of view of the sensors in reverse order, allowing the sensors to capture and record the time of passage to a memory, such as a counter timer board.

It may be desirable to operatively connect a processing device to at least part of the apparatus, such as the sensors. The processing device is preferably capable of housing the memory and a processor that is capable of determining the COR and contact time of the collision, based on the times recorded by the sensors. The present invention allows the COR of the material sample to be tested based on a reusable projectile. Furthermore, the present invention may use material samples with a wide range of thicknesses and cross sections. For example, the specimen may be cylindrical or rectangular and material thickness may range from 1/8" to 2". This substantially simplifies the testing process and increases the type of material samples which may be used. The present invention also measures resilience gradients of anisotropic material specimens. This may be accomplished by targeting different locations on the material specimens. Different locations on the material sample may be targeted by moving the sample, moving the tubular barrel, or moving both. The present invention provides the added benefit of occupying a smaller amount of space than prior apparatus by minimizing the distance between the tubular barrel and the material sample.

As mentioned above, the present invention comprises an apparatus that is capable of measuring the COR and contact time. This is preferably achieved by propelling a projectile towards the substantially stationary material sample. In one embodiment, the projectile may be used repeatedly to test a plurality of material samples as long as it maintains its structural integrity. The elastic modulus of the projectile may be greater than 50 times greater than the elastic modulus of the material sample.

In one embodiment, the projectile may comprise a metal, plastic, or ceramic. In one embodiment, this may be accomplished by forming the projectile from one or more metals, such steel, tungsten, iron, titanium, aluminum, or alloys, and the like. In embodiments where the material sample is substantially soft, it may be desirable to form the projectile using plastics. However, in embodiments where the material sample is substantially hard, it may be desirable to form the projectile using another material, such as a metal or the like. In any embodiment, it is desirable for the elastic modulus of the projectile to be at least 50 times greater than the elastic modulus of the material sample.

In one embodiment, the projectile comprises a substantially spherical shape. In some embodiments, the density of the spherical projectile may be varied in order to vary the amount of material deformation during the collision. In some embodiments, the spherical projectile may be a hollow sphere. In other embodiments, the spherical sample may be a solid sphere. When the spherical projectile is a solid sphere, the density of the spherical projectile may be between about 0.01 and 0.90 lb/sq. in$^3$. Table 1, below, shows the density and elastic modulus of some exemplary materials that may be used to form the projectile.

TABLE 1

| Material | Density (Lb/in$^3$) | Elastic Modulus (psi) |
| --- | --- | --- |
| Acrylic | 0.05 | 4.3E + 05 |
| Alumina-Ceramic | 0.13 | 5.5E + 07 |
| Aluminum | 0.10 | 1.1E + 07 |
| Steel | 0.29 | 2.9E + 07 |
| Titanium | 0.16 | 1.5E + 07 |
| Tungsten | 0.70 | 5.0E + 07 |

As mentioned above, the projectile may be formed using any material, provided that the elastic modulus is at least 50 times greater than the elastic modulus of the material sample. Regardless of the material or materials used, the projectile is preferably formed such that its properties do not change over time.

The size of the projectile may also be varied. In embodiments where the projectile is substantially spherical, the size of the projectile may be described according to its diameter. Preferably, the diameter of the sphere is between about 0.0625" and about 1.0". More preferably, the diameter of the sphere may be between about 1/8" and about 1/4".

As mentioned above, it may be desirable to determine the characteristics of the projectile such that it is capable of maintaining its structural integrity despite repeatedly striking one or more material samples. Accordingly, it may be desirable for the elastic modulus of the projectile to be substantially greater than the elastic modulus of the material sample. This allows the projectile to maintain its structural integrity after a plurality of impacts with one or more material samples. Preferably, the elastic modulus of the projectile is about 50 times greater than the elastic modulus of the material sample. More preferably, the elastic modulus of the projectile may be about 75 times greater, and most preferably the elastic modulus of the projectile may be about 100 times greater than the elastic modulus of the material sample. Another way to describe the elastic modulus of the projectile relative to the material sample is by a ratio. Preferably, the ratio of the elastic modulus of the projectile to the elastic modulus of the material sample is greater than about 50:1. More preferably, the ratio may be greater than about 75:1, and most preferably the ratio of the elastic modulus of the projectile to the elastic modulus of the material sample may be greater than about 100:1.

As mentioned above, the projectile may be substantially spherical, and may vary in its density, size, and elastic modulus. In a preferred embodiment, the characteristics of the projectile may be chosen such that the projectile is capable of maintaining its structural integrity after repeated impacts with one or more material samples. One advantage of a reusable spherical projectile is that the testing process may be substantially automated. For example, in one embodiment, the present invention comprises a processing device, such as a computer, Programmable Logic Controller (PLC), or the like. In addition, the present invention may include associated tooling and mechanisms that may be used to perform testing in a fully automated fashion. It may be desirable to include a user interface capable of being accessed through a computer terminal to provide information required to begin testing. This information may include, but is not limited to, a test name, sample designation, number of test cycles, and multiple velocity settings. Other interface controls may include Start, Stop, Pause, Re-test, and the like.

In one embodiment, the PLC may be capable of controlling various aspects of the testing process. For example, the PLC may control the air pressure to control the velocity of the projectile. In such an embodiment, the material sample may be positioned in a desired location within the holding slot. A mass plate may then be moved into position behind the material sample. At substantially the same time, the tubular barrel may be shuttled forward and back to load the projectile. Once this occurs, the projectile may be fired at target. Sensors capture the precise passage of the projectile prior to and after impact with the material sample. Once the impact has occurred, the projectile is removed from impact chamber and recycled to tubular barrel. Preferably, automation continues for the duration of the test or for however many cycles were selected based on the user interface.

In one embodiment, the results of the impact, such as the calculated COR and contact time, as discussed in more detail below, may be summarized in a report that may be accessed through the computer terminal. The results may include information such as velocities, COR, contact time, slope of contact time, slope of COR, averages and standard deviations of this data, and the like.

As described above, the projectile is preferably aimed and fired through a tubular barrel towards the material sample. The tubular barrel preferably includes a propulsion system. In one embodiment, the propulsion system may control pneumatic energy via a pneumatic valve. In a preferred embodiment, the projectile may be fired out of the tubular barrel pneumatically. In a preferred embodiment, the pressurized air may be stored in a pressurized air tank. The volume of the air tank is preferably, for example, at least twice the volume of the tubular barrel. More preferably, the volume of the tank is at least three times the volume of the tubular barrel.

The air pressure may be adjusted by using one or more pressure gauges and regulators. It is sometimes desirable to determine the COR and contact time of a material sample at alternate projectile velocities. In these applications, an adjustable regulator may be desirable.

In one embodiment, the propulsion system may be capable of imparting a desired speed to the projectile. It is preferred that the speed imparted to the projectile is sufficient to allow the projectile to strike the material sample and rebound back through the field of view each of the sensors. This provides the advantage of allowing the COR and contact time of the collision to be accurately and precisely calculated. When measuring the COR of a material, it may be desirable to use a propulsion system that is both accurate and repeatable. In addition, it may be desirable for the propulsion system to impart substantially the same speed to the projectile each time it is propelled towards the material sample. This ensures that the COR and contact time of a given sample will be substantially the same each time it is tested. In one embodiment, the repeatability of the propulsion system may be described according to its precision. In other words, the propulsion system may be described according to its ability to impart substantially the same velocity to the projectile each time it is propelled through the tubular barrel. In one embodiment, the propulsion system may be capable of propelling the projectile within 5 feet per second or less of a desired velocity each time it is fired. Preferably, the propulsion system is capable of propelling the projectile such that it is capable of striking the material sample within 0.1" or less of the desired contact point.

In another embodiment, the precision may be measured by propelling the projectile through the tubular barrel a given number of times, for example, 10 times. The difference between the highest and lowest velocity may then be measured. Preferably, the difference between the highest and lowest velocity of the projectile is 10% or less. More preferably, the difference between the highest and lowest velocity is about 7% or less, and most preferably the difference between the highest and lowest velocity is about 4% or less. Another way to describe the precision of the propulsion system is to measure the difference between the velocities of the projectile from any two consecutive firings. Preferably, the difference between the velocities of the projectile from any two consecutive firings may be between about 0 and about 10%. More preferably, the difference between the velocities may be between about 2 and about 8%, and most preferably the difference between the velocities of the projectile from any two consecutive firings may be between about 4 and about 6%.

As mentioned above, it may be desirable for the propulsion system to impart a velocity to the projectile that allows it to rebound off the material sample and pass through the field of view of each of the sensors. Preferably, the propulsion system imparts a velocity between about 20 fps and 200 fps.

In one embodiment, the tubular barrel comprises a single barrel whose diameter may be chosen based on the size of the projectile. In a preferred embodiment, the inner diameter of the tubular barrel may be between 0.001 and 0.080" greater than the diameter of the projectile. More preferably, the inner diameter of the tubular barrel may be between 0.038 and 0.080" greater than the diameter of the projectile.

In a preferred embodiment, the tubular barrel is substantially horizontal. After being fired out of the tubular barrel, the projectile may pass through two or more sensors and impacts the material sample. In one embodiment, the passage of the projectile may be detected based on at least two sensors. The two sensors are preferably placed at predetermined positions between the end of the tubular barrel and the material sample. It is desired that the at least two sensors are able to detect the position of the projectile as it passes from the tubular barrel towards the material sample, and again as it rebounds off of the material sample and back through the sensors. The sensors are preferably capable of accurately and precisely detecting the passage of a fast moving projectile. Accordingly, any sensor that is known to those skilled in the art may be used. For example, the sensors may have LED's or light emitting devices and receiving lenses. Alternately, the sensors may be infrared LED through-beam sensors. Infrared LED sensors typically have a long life span, require less maintenance, and are more accurate when used to detect low speed objects. The sensors may be arranged in any manner to allow sensing of an object passing through a predetermined plane. In a preferred embodiment, it may be desirable to use two STM Optical Frame Sensors, Model No. RLS/S 118-080-080-ADP, or the like. The sensors that are used to detect the passage of the projectile may do so using any desired method. This may include detecting the passage of the projectile including, but not limited to, optical, magnetic, or capacitance variations that are generated due to the presence of the projectile.

In a preferred embodiment, two sensors are used to detect the passage of the projectile. One way to describe the positioning of the sensors is by the distance between the two sensors. Preferably, the distance between the two sensors is between about 0 and about 5 feet. More preferably, the distance between the two sensors is between about 6" and about 12". Another way to describe the positioning of the sensors is by the distance between the closest sensor and the projectile exiting edge of the tubular barrel. Preferably, the distance between the closest sensor and the projectile exiting edge of the tubular barrel is about 5 feet or less. More preferably, the distance between the closest sensor and the projectile exiting edge of the tubular barrel is about 1 foot or less, and most preferably the distance between the closest sensor and edge of the tubular barrel is about 6" or less. Another advantage of having a space between the tubular barrel and the sensors is that the effect of air pressure from the barrel changing the velocity of the projectile may be minimized.

One way to determine the COR of the material sample is to measure the time of passage of the projectile based on the sensors described above. In one embodiment, it may be desirable to operatively connect a timing device to record the passage of the projectile recorded by each sensor. In one embodiment, the timing device may be a separate element. However, in a preferred embodiment the timing device may be part of a computing device processor or controller. In a preferred embodiment, it may be desirable to use a counter timer board that may be housed within the computing device. The counter timer board allows the computing device to determine the exact time of passage of the projectile and store it in a memory. The memory may be a separate element, but more preferably it may be operatively connected to the computing device. In one embodiment, the computing device includes a processor capable of performing mathematical calculations such as calculating the coefficient of restitution and contact time.

Figure 3:
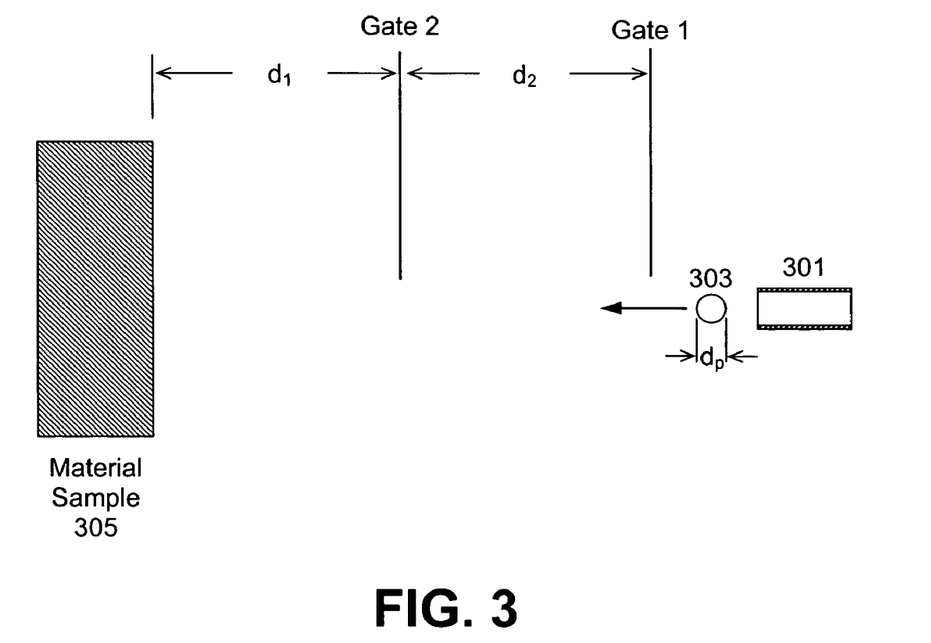
FIG. 3 is a diagram showing one embodiment that may be used to determine physical properties of a material sample, such as coefficient of restitution and contact time.

The COR may be calculated based on the position of the two sensors relative to the material sample and the tubular barrel. Referring to FIG. 3, one method of determining COR and contact time is discussed. In one embodiment, the projectile 303 is fired out of the tubular barrel 301 towards the material sample 305. Two gates are positioned between the tubular barrel 301 and the material sample 305. The inbound velocity of the projectile is $d_2/(t_{1-2})$. The outbound velocity of the projectile is $d_2/(t_{2-1})$. The COR of the material sample may be determined by $V_{out}/V_{in}$. The contact time of the projectile may be determined by $t_{2-2}-(d_1/V_{in})-((d_1-d_p)/V_{out})$. Where $d_p$ is the diameter of the projectile.

The relationship between COR of the material sample and the projectile velocity varies in a substantially linear manner. In one embodiment, the most reliable method of determining the COR of a material sample is to test the sample using two substantially different projectile velocities. A graph may then be created using a slope of velocity vs. COR. COR values at any other reference velocity may then be calculated. Preferably, the two substantially different velocities are not so far apart that they result in a graph that is not linear. Preferred velocities for firing the projectile are about 110 and about 140 fps. COR at a preferred reference velocity of 125 fps may then be calculated. This method of calculating COR is well known to those skilled in the art.

In other embodiments, other algorithms and methods of calculating the COR of a material may be used. For instance, another algorithm for calculating the COR of a material is described in U.S. patent application Ser. No. 10/428,750, and may be used to calculate the COR of the material sample according to the present invention.

In some embodiments, the present invention may be used to measure the contact time between the projectile and the stationary material sample and the COR simultaneously. In one such embodiment, a sensing device, such as a light gate or the like, may be selectively positioned in such a way that the sensing plane is parallel to the striking surface of the material sample. Preferably, the distance between the sensing plane and the striking surface is greater than the dimension of the projectile. The sensing device is preferably able to detect the passage of the ball. In one embodiment, the sensing device may determine when the leading edge and the back edge of the projectile enter and leave the sensing plane. This may occur when the projectile is traveling towards the material sample and after the projectile rebounds off the material sample. In this way, the contact time of the projectile and the material sample may be detected. Thus, the contact time may be measured substantially simultaneously with the COR. Many different sensors, sensor arrangements, and methods for determining contact time may be employed, as discussed in U.S. Pat. No. 6,571,600, the entirety of which is incorporated herein by reference.

As mentioned above, the projectile strikes the material sample and rebounds away from it. Thus, in one embodiment it may be desirable to ensure that the material sample has uniform properties. The material sample may comprise any shape, for example, circular, square, triangular, hemispherical, and the like. In order to ensure that the projectile rebounds from the material sample in a predictable manner, it may be desirable for it to have a uniform surface texture. In one embodiment, the surface texture of the material sample is preferably substantially smooth, non-porous, free of protrusions, cavities, cracks, holes, and the like.

In one embodiment, the thickness of the material sample may be varied as desired. For example, in one embodiment the thickness of the material sample may be chosen such that the material sample is able to absorb a majority of the energy that is transferred to it when the projectile impacts it. In such an embodiment, the material sample may be substantially thin when it comprises a hard material. Conversely, the material sample may be substantially thicker when it comprises a soft material. Preferably, the thickness of the material sample is between about 0.1" and 2". More preferably, the thickness of the material sample is between about ¼" and about ½".

In order to allow the projectile to strike the material sample and rebound off of it, it is desirable for the material sample to be substantially stationary. In one embodiment, this may be achieved by using a holding device. As mentioned above, the holding device may include a mass backing that is about 100 times or more greater than the mass of the projectile. In other words, the mass of the backing is preferably substantially greater than the mass of the material sample. More preferably, the mass of the backing may be about 150 times or more greater than the mass of the material sample. Most preferably, the mass of the backing may be about 200 times or greater than the mass of the material sample.

In one embodiment, the infinite mass backing may comprise any material, such as a metal, plastic, alloy, and the like. The metal may include, but is not limited to, steel, iron, titanium, aluminum, and the like. In one embodiment, the mass backing comprises an opposing holding slot and a mass backing, as described above. In other embodiments, the surface area of the mass backing that is in contact with the material sample is at least as large as the surface area of the material sample. In this embodiment, the shapes of the surface area of the mass backing and the material sample are substantially similar. In other embodiments, the mass backing may comprise any shape, as long as the surface area of the backing that is in contact with the material sample is substantially larger than the surface area of the material sample. Preferably, the surface area of the mass backing is about 10 times the surface area of the material sample. More preferably, the surface area of the mass backing may be about 5 times the surface area, and most preferably the surface area of the mass may be about 1.25 times the surface area of the material sample.

In a preferred embodiment, the projectile leaves the tubular barrel and strikes the material sample. The tubular barrel is preferably positioned such that the projectile strikes the material sample at a predetermined distance from the edge of the sample. One way to describe the predetermined distance is according to the diameter of the projectile. Preferably, the tubular barrel is positioned such that the distance between the impact area and the edge of the material sample is at least 1.5 times the diameter of the projectile. More preferably, the tubular barrel is positioned such that the distance between the impact area and the edge of the material sample is at least twice the diameter of the projectile.

In a preferred embodiment, the material sample may be located at an angle with respect to the tubular barrel. Preferably, the angle between the tubular barrel and the material sample is substantially close to about 90 degrees to avoid placing spin on the rebounding projectile. However, the angle should be chosen so that the projectile is prevented from rebounding off of the material sample and re-entering the tubular barrel. Preferably, the angle of the material sample with respect to the tubular barrel may be between about 85 and about 95 degrees.

The present invention may be used with additional apparatus for returning or recycling the projectile after it rebounds off of the material sample. Such apparatus involve placing the sensors and the material sample into a chamber. The end of the tubular barrel from which the projectile exits would also be enclosed, at least partially, by the chamber. Once the projectile is fired and rebounds off the material sample, it may be captured and fed back into the tubular barrel. One such method is described in U.S. patent application Ser. No. 10/428,750.

In one embodiment, the material sample may be manufactured using any desired method or apparatus. For example, in one embodiment the material sample may be manufactured based on injection molding, a cast, press, and the like. Prior art methods for manufacturing molds have several limitations. For example, prior art apparatus involve forming a material sample using, for example, three plates. These apparatus typically comprise a top, middle, and bottom plate. In order to remove a molded article, the plates must be manually separated by an operator using, for example, a sharp device to for separation of the plates. Once the plates are separated, an operator may remove the molded sample. One disadvantage of prior art apparatus is the time and effort required to separate the plates. Another disadvantage of prior art apparatus is that the plates may be damaged by using a sharp device to separate the plates.

Figure 2A:
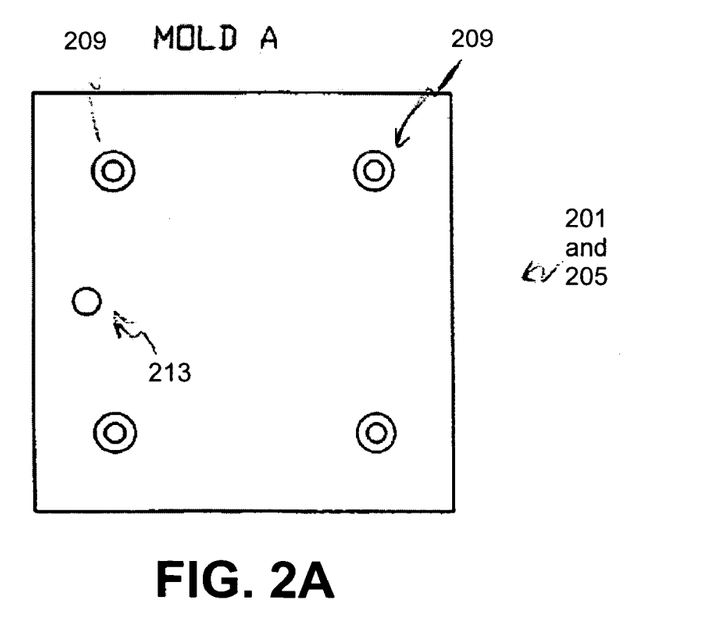
FIGS. 2A–2c illustrate one embodiment of mold plates according to the present invention.
Figure 2B:
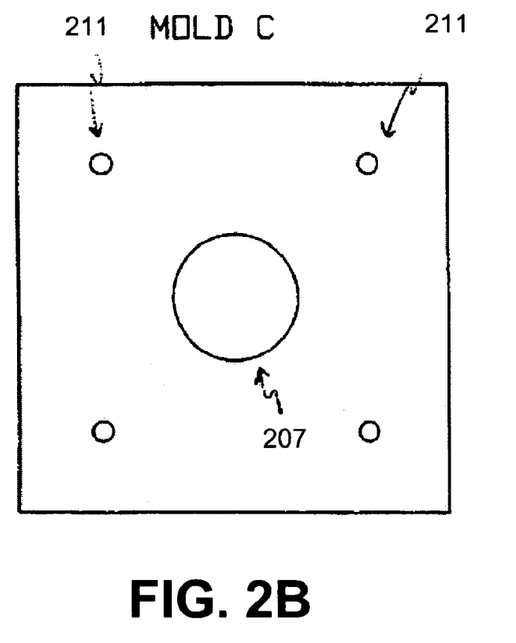
Figure 2C:
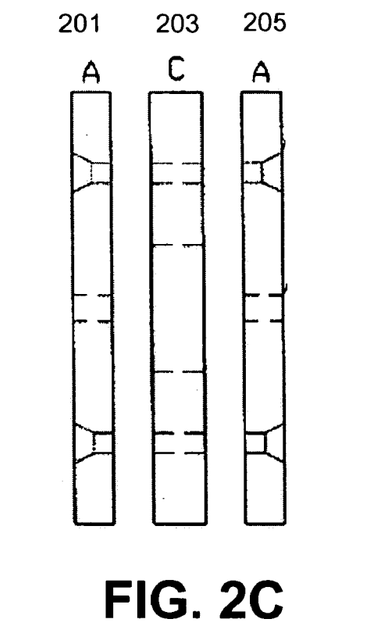

In one embodiment, shown in FIGS. 2A–2C, the present invention includes three molding plates 201–205. The three plates may be positioned as shown in FIG. 2C, with plate 203 positioned in between plates 201 and 205. Preferably, plates 201 and 205 are substantially similar. Plate 203 preferably comprises a cavity 207 for forming a molded sample. In one embodiment, the shape of the cavity 207 may be circular. Plates 201–205 may be pressed together to form a molded sample in cavity 207, using for example, heat and pressure. In order to predictably and repeatably align the plates 201–205, one or more openings 209–211 may be included. Preferably, the openings 209–211 are selectively positioned at desired points on plates 201–205. The openings 209–211 preferably allow for the insertion and passage of an alignment device, such as a pin or screw. In one embodiment, the alignment devices preferably pass at least partially into corresponding openings 211, allowing the plates 209–211 to be aligned in a desired manner.

As mentioned above, prior art apparatus typically require the plates 201–205 to be manually separated. However, in one embodiment, plates 201–205 preferably comprise an additional opening 213 that may be positioned towards the periphery of the plates 201–205. As shown in FIGS. 2A and 2C, one advantage of this positioning may be that the opening is not as likely to be filled by any excess material that may be forced out of the cavity 207 during formation of the molded sample. In one embodiment, there are no corresponding openings positioned on plate 203. This allows a separation device, such as a screw, to be inserted into the openings 213. In one embodiment, the opening may be threaded to facilitate the insertion of the screw. After the sample has been molded, the screw may be inserted into the opening 213. As the screw is inserted into the opening, it exerts a downward force on plate 203. This force preferably causes the separation of the plates, allowing an operator to remove the molded sample from the cavity 207.

According to the method of the present invention, the COR of a material is tested using, for example, a projectile having predetermined properties such as size, shape, density, elastic modulus, hardness, and the like. The projectile is preferably capable of being used a plurality of times to test one or more material samples. In one embodiment, the projectile may be placed into a tubular barrel. The tubular barrel may be operatively connected to a propulsion system that is capable of firing the projectile out of the tubular barrel at a predetermined velocity. In order to determine the COR of the material sample, the tubular barrel is preferably aimed such that a fired projectile will strike the material sample.

It is desirable to selectively position two or more sensors between the exiting edge of the tubular barrel and the material sample. In one embodiment, the two sensors may be placed at precise discrete locations in order to record the passage of the projectile. Upon the projectile passing through each sensor, time is recorded to, for example, a counter timer board. The projectile then impacts the material sample that is held in place by, for example, a holding slot backed by, for example, an infinite mass cylinder. The holding slot and infinite mass prevent the material sample from moving, and allow the projectile to rebound off of the material sample. The projectile may then rebound outbound from the material sample, back through the sensors, in reverse order. In a preferred embodiment, the sensors may capture the time of passage of the projectile and record it to a counter timer board.

In one embodiment, the recorded inbound and outbound times of the projectile passage, along with the known precise sensor locations, may be used to calculate the inbound and outbound velocities of the projectile. This information may be processed by a computer processor or controller in order to calculate the coefficient of restitution using, for example, an algorithm.

Figure 4A:
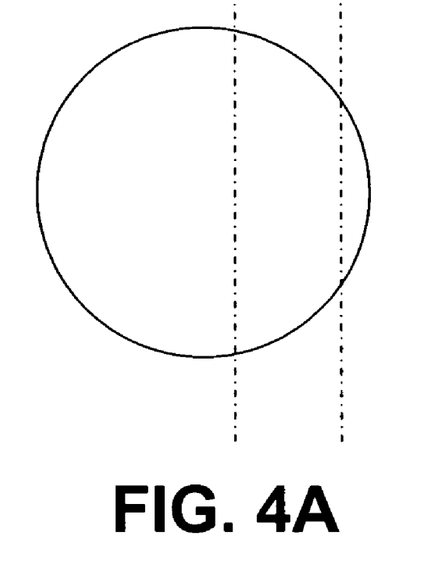
FIGS. 4A–4C are diagrams showing exemplary sections of a golf ball that may be tested according to the present invention.
Figure 4B:
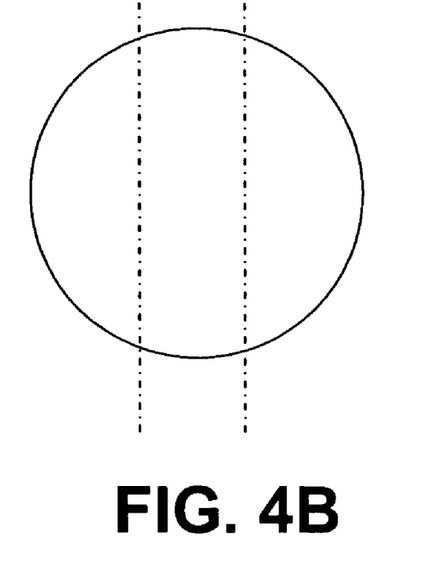
Figure 4C:
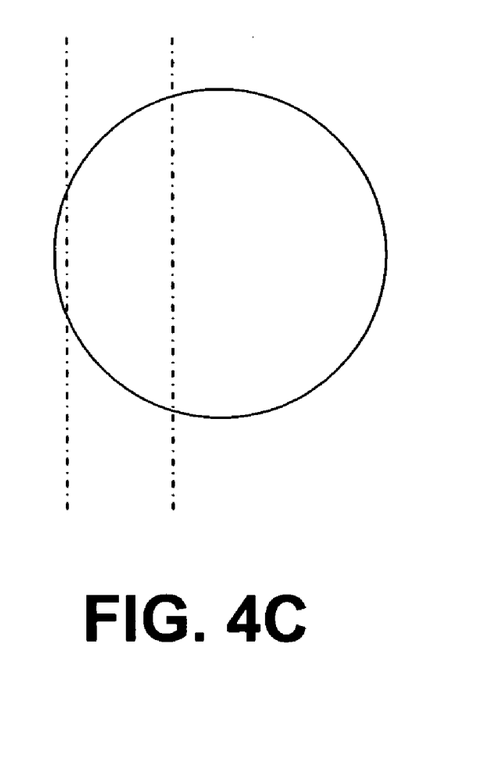
Figure 5A:
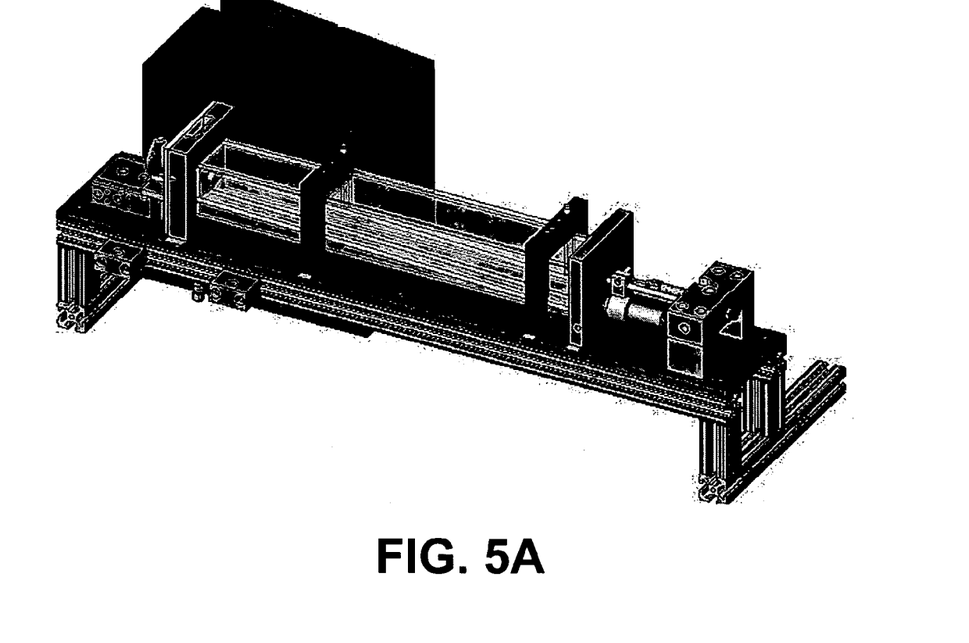
FIGS. 5A–5C are illustrations of one embodiment of a device for testing properties of a material sample.
Figure 5B:
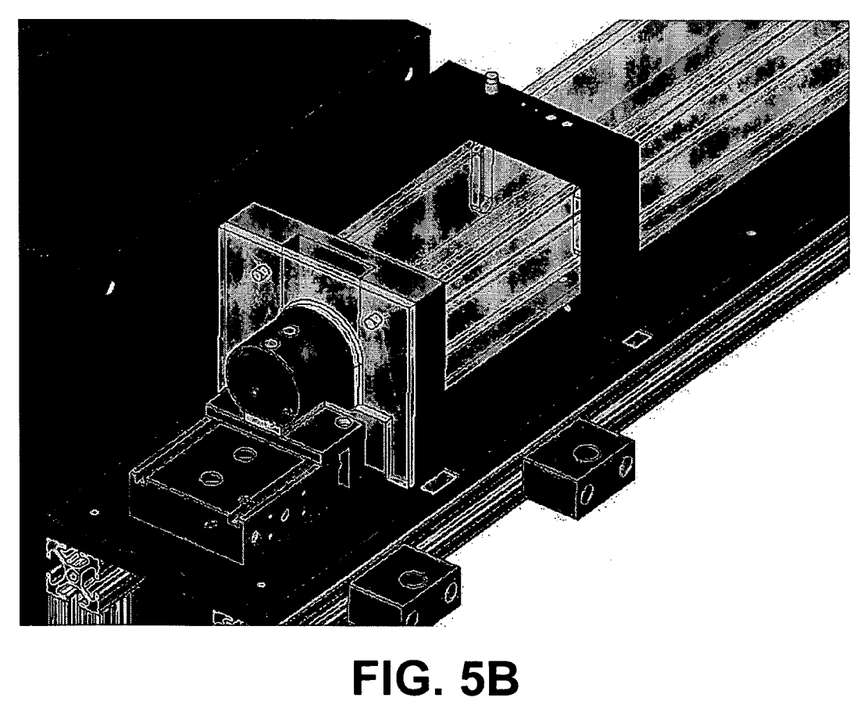
Figure 5C:
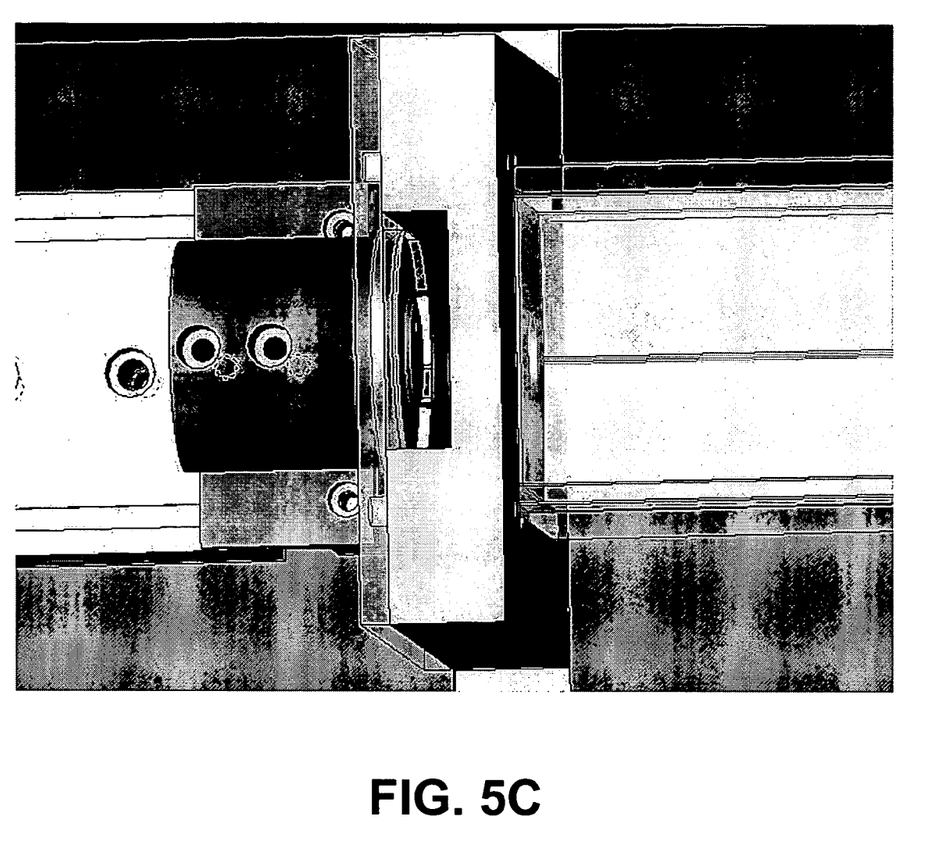

Golf ball manufacturers are continuously seeking methods of improving golf ball performance. One aspect of golf ball design which significantly effects performance is the anisotropy of a golf ball core. Golf ball designers control the anisotropy of the golf ball with alternative chemical constituents and thermal conditions employed in the core forming process. This apparatus allows the golf ball designer to section a golf ball or its core or other component and measure the anisotropy for that section of material. As shown in FIGS. 4A–4C, anisotropic properties of a golf ball may be determined based on a portion of a golf ball or golf ball component. Any section of the golf ball may be used. Once a portion of the golf ball has been isolated, either surface of the section may be used as an impact surface for the projectile. In this manner, the anisotropic properties of any portion of the golf ball may be determined.

Although the present invention has been described with reference to particular embodiments, it will be understood to those skilled in the art that the invention is capable of a variety of alternative embodiments within the spirit of the appended claims.

The invention claimed is:

1. An apparatus for determining the characteristics of a mechanical collision, comprising:

a holding device capable of receiving and holding a stationary material sample;

a projectile;

a propulsion device capable of propelling the projectile towards the stationary material sample;

at least two sensors selectively positioned between the propulsion device and the stationary material sample, wherein the sensors are capable of measuring the time and position of the outbound movement of the projectile; and a processor operatively connected to at least one of the holding device, the propulsion device, and the at least two sensors, wherein the characteristics of the mechanical collision are determined automatically by the processor.

2. The apparatus according to claim 1, wherein the projectile comprises a metallic sphere.

3. The apparatus according to claim 2, wherein the diameter of the sphere is between about 0.0625" and about 0.5".

4. The apparatus according to claim 2, wherein the diameter of the sphere may be between about 0.125" and about 0.250".

5. The apparatus according to claim 1, wherein the elastic modulus of the projectile is at least about fifty times greater than the elastic modulus of the sample.

6. The apparatus according to claim 1, wherein at least one sensor is positioned less than about 6" or greater from the end of the propulsion device.

7. The apparatus according to claim 1, wherein the processor comprises a programmable logic controller.

8. The apparatus according to claim 1, wherein the material sample is backed by a mass which is 100 times greater than the mass of the projectile.

9. The apparatus according to claim 1, wherein the weight of the projectile is between about 0.200 grams and about 0.600 grams.

10. The apparatus according to claim 1, wherein the processor is capable of determining the COR of the material sample.

11. The apparatus according to claim 10, wherein the processor is capable of determining the contact time of the projectile.

12. The apparatus according to claim 1, wherein the propulsion device comprises a pneumatic valve.

13. The apparatus according to claim 1, further comprising a tubing system capable of capturing the projectile after it strikes the material sample and returning it to the propulsion device.

14. The apparatus according to claim 1, further comprising a user interface.

15. The apparatus according to claim 1, wherein the processor is capable of determining at least one of:

velocity;

COR;

contact time;

slope of contact time;

slope of COR; and averages and standard deviations of COR or contact time.

16. The apparatus according to claim 1, wherein the propulsion device is capable of propelling the projectile within 5 fps of a predetermined velocity.

17. The apparatus according to claim 1, wherein the propulsion device is capable of propelling the projectile to strike the material sample within 0.1" of a predetermined point on the material sample.

18. The apparatus according to claim 1, wherein the projectile comprises one of steel, aluminum, tungsten, acrylic, titanium, or ceramic.

19. A method for determining the characteristics of a mechanical collision, comprising:

providing a stationary material sample;

firing an object at the stationary material sample;

automatically determining the inbound and outbound characteristics of the flight of the object; and automatically correlating the ratio of inbound and outbound characteristics to a property of the stationary material sample.

20. The method according to claim 19, wherein the inbound and outbound characteristics comprise inbound velocity and outbound velocity.

21. The method according to claim 19, wherein the automatically correlating comprises determining the COR of the stationary material sample.

22. The method according to claim 19, further comprising automatically determining the contact time of the object based on the inbound and outbound characteristics of the flight of the object.

23. The method according to claim 19, wherein the firing comprises propelling the object at the sample at a velocity between about 50 fps and 200 fps.

24. The method according to claim 19, wherein the firing comprises propelling the object at the sample at a velocity between about 85 and 175 fps.

25. The method according to claim 19, wherein the inbound and outbound characteristics comprises the time of passage of the object.

26. The method according to claim 19, wherein the material sample comprises a section of a golf ball.

27. The method according to claim 19, wherein the automatically correlating comprises determining the anisotropic characteristics of the material sample.

28. A method for determining the characteristics of a mechanical collision, comprising:

automatically selectively positioning a stationary material sample at a predetermined distance from a projectile;

selectively positioning at least two sensors responsive to the presence of the projectile;

propelling the projectile towards the stationary material sample; and automatically determining the COR of the stationary material sample based on the at least two sensors and the projectile.

29. The method according to claim 28, wherein the projectile is propelled towards the material sample at a velocity between about 50 fps and 200 fps.

30. The method according to claim 28, wherein the projectile is propelled towards the material sample at a velocity between about 85 and 175 fps.

31. The method according to claim 28, wherein the determining is based on the velocity of the projectile.

32. The method according to claim 28, wherein the determining is based on the time of passage of the projectile.

33. The method according to claim 28, wherein the at least two sensors are responsive to the presence of the projectile based on optical sensing.

34. The method according to claim 28, wherein the at least two sensors are responsive to the presence of the projectile based on magnetic variations.

35. The method according to claim 28, wherein the at least two sensors are responsive to the presence of the projectile based on capacitance variations.

36. The method according to claim 28, further comprising automatically determining the contact time of the projectile based on the at least two sensors.

37. The method according to claim 28, wherein the automatically determining comprises determining the anisotropic properties of a golf ball section.

38. The method according to claim 28, wherein the propelling comprises propelling the projectile at a velocity within about 5 fps of a predetermined velocity.

39. The method according to claim 28, wherein the projectile is capable of striking the material sample within about 0.1" of a predetermined point on a material sample.

40. The method according to claim 39, wherein the density of the projectile is between about 0.01 and about 0.90 lb/sq. in$^3$.

* * * * *